United States Patent [19]
Pages et al.

[11] Patent Number: 5,971,948
[45] Date of Patent: Oct. 26, 1999

[54] APPARATUS FOR COLLECTION, WASHING, AND REINFUSION OF SHED BLOOD

[75] Inventors: Etienne Pages, Saint Avertin; Jean Papillon, St. Germain-En-Laye, both of France

[73] Assignee: Haemonetics Corporation, Braintree, Mass.

[21] Appl. No.: 08/818,314

[22] Filed: Mar. 14, 1997

Related U.S. Application Data

[62] Division of application No. 08/571,496, Dec. 13, 1995, Pat. No. 5,643,193.

[51] Int. Cl.$^6$ .................................................. A61M 37/00
[52] U.S. Cl. ............................................. 604/6; 210/645
[58] Field of Search ........................... 604/4–6; 210/781, 210/782, 645

[56] References Cited

U.S. PATENT DOCUMENTS

| | | | |
|---|---|---|---|
| 3,645,252 | 2/1972 | Gilford | 128/2 |
| 3,655,123 | 4/1972 | Judson et al. | 233/21 |
| 3,965,896 | 6/1976 | Swank . | |
| 4,086,924 | 5/1978 | Latham, Jr. . | |
| 4,189,470 | 2/1980 | Rose . | |
| 4,321,192 | 3/1982 | Jain . | |
| 4,411,786 | 10/1983 | Russell . | |
| 4,416,654 | 11/1983 | Schoendorfer et al. . | |
| 4,668,214 | 5/1987 | Reeder . | |
| 4,872,988 | 10/1989 | Culkin | 210/636 |
| 4,886,487 | 12/1989 | Solem et al. . | |
| 5,055,198 | 10/1991 | Shettigar | 210/650 |
| 5,147,290 | 9/1992 | Jonsson . | |
| 5,182,019 | 1/1993 | Cote et al. | 210/321.8 |
| 5,215,519 | 6/1993 | Shettigar . | |
| 5,234,403 | 8/1993 | Yoda et al. . | |
| 5,238,655 | 8/1993 | Laible et al. | 422/101 |
| 5,294,401 | 3/1994 | Hagiwara | 422/48 |
| 5,298,016 | 3/1994 | Gordon . | |
| 5,311,908 | 5/1994 | Barone et al. . | |
| 5,378,227 | 1/1995 | O'Riordan et al. . | |
| 5,386,734 | 2/1995 | Pusinelli . | |
| 5,411,472 | 5/1995 | Steg, Jr. et al. . | |
| 5,419,759 | 5/1995 | Naficy | 604/5 |
| 5,423,738 | 6/1995 | Robinson et al. . | |
| 5,643,193 | 7/1997 | Papillon et al. | 604/6 |

FOREIGN PATENT DOCUMENTS

| | | |
|---|---|---|
| 95/03840 | 2/1995 | European Pat. Off. . |
| 0 682 953 A1 | 5/1995 | European Pat. Off. . |
| WO89/01792 | 3/1989 | WIPO . |
| WO94/21311 | 9/1994 | WIPO . |

*Primary Examiner*—John G. Weiss
*Assistant Examiner*—Ki Yong O
*Attorney, Agent, or Firm*—Cesari and McKenna, LLP

[57] ABSTRACT

An integrated, vacuum-driven shed blood processing system that collects, dilutes, filters and washes postoperatively shed blood and concentrates red blood cells for reinfusion to the patient. The location of the centrifuge bowl between the surgical site and the vacuum source used to clean the site allows the immediate collection of shed blood in the bowl without an intermediate reservoir or an additional pump. In conjunction with a modified centrifuge bowl having a sealed aperture in its floor that permits reinfusion directly from the bowl without an additional reinfusion bag or reverse pump, this configuration processes blood for reinfusion using fewer steps and components yet without loss of functionality. Dilution of the blood upon its introduction into the system reduces the tendency to coagulate and allows the use of lower bowl rotation speeds. Slower rotation reduces red blood cell damage and lowers power requirements, which improves portability.

25 Claims, 3 Drawing Sheets

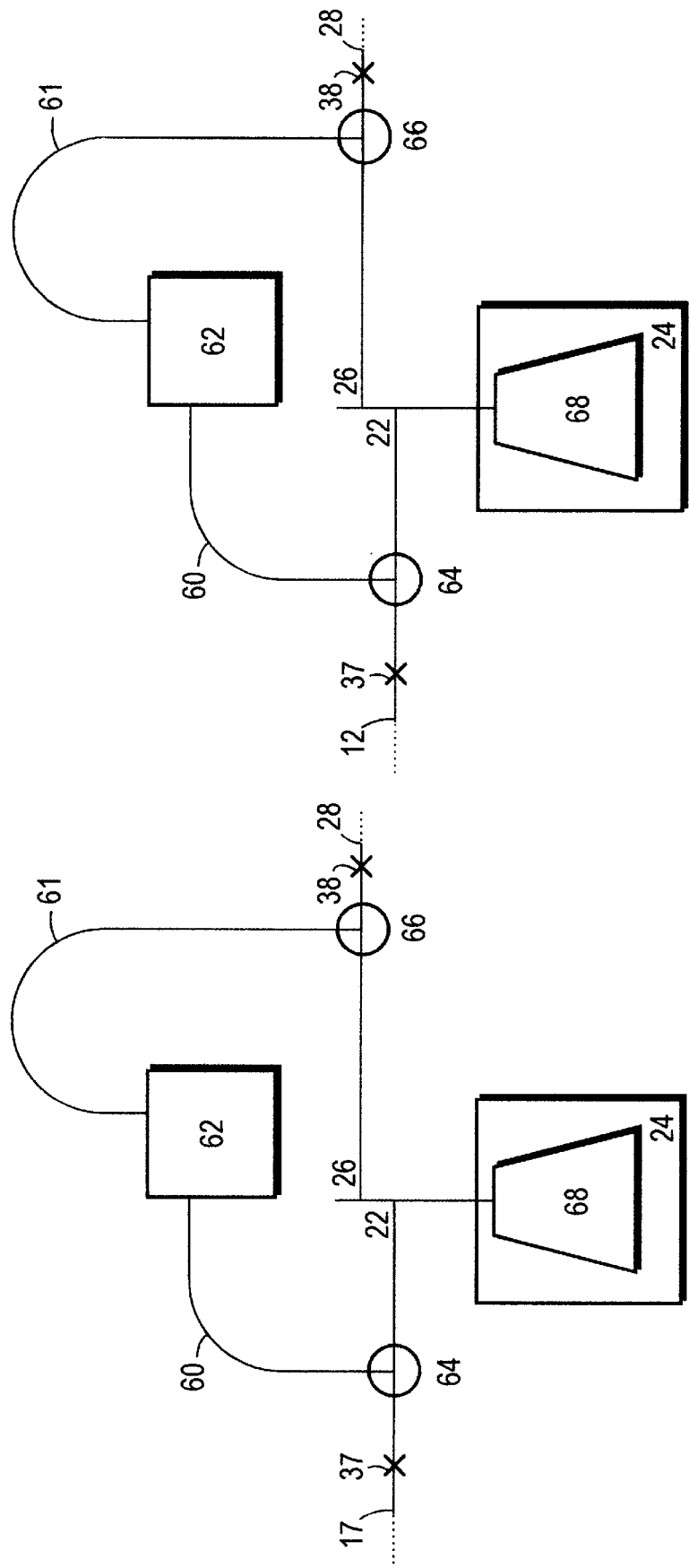

APPARATUS FOR COLLECTION, WASHING, AND REINFUSION OF SHED BLOOD

This is a division of U.S. Ser. No. 08/571,496 filed Dec. 13, 1995 now U.S. Pat. No. 5,643,193.

FIELD OF THE INVENTION

This invention relates to blood processing. Particularly, this invention relates to methods and apparatus for collecting and washing postoperatively shed blood for reinfusion into the patient.

BACKGROUND OF THE INVENTION

Recovery and reinfusion of blood lost due to surgery rather than transfusion of donor blood preserves blood bank resources and eliminates the risk of transmitting infection and of adverse reaction due to donor incompatibility. Even when the amount of blood lost does not indicate transfusion, recovery and return of shed blood can benefit the patient.

Conventionally, shed blood is collected intraoperatively from an open surgical site using a hand-held suction wand. Postoperatively, a drainage tube under controlled suction removes blood from the closed cavity. The required suction is routinely provided by vacuum pumps because of the easily regulated negative pressure they provide and their relative low cost compared to other types of pumps.

U.S. Pat. No. 3,965,896 discloses an apparatus that withdraws blood from a surgical site by vacuum, filters it, adds an anticoagulant, and delivers the admixed blood to a reservoir from which it can be reinfused into the patient. Although the filtration removes blood clots and fragments of bone and other tissue, it leaves anticoagulant, cellular debris, toxins, and irrigation fluid in the blood. These elements should preferably be removed before reinfusion. Also, withdrawal of the lighter blood components, such as plasma and white blood cells, and reinfusion of only the red blood cells helps reduce bleeding.

For these reasons, it is desirable to wash the shed blood and concentrate the red blood cells following filtration and anticoagulation. Centrifugation is a commonly applied technique for performing these tasks. A typical centrifuge bowl for this application is the so called Latham bowl, described in U.S. Pat. No. 4,300,717. Blood enters through an inlet tube into a separation chamber. Rotation of the bowl separates blood in the separation chamber into its components according to density, with the red blood cells collecting at the periphery of the bowl and the various lighter components forming concentric cylinders of successively smaller radii. As the bowl fills, the red blood cells displace the lighter components, concentrated near the center, out of the bowl through an exit port to a waste receptacle. A saline washing solution may then be added to enhance segregation of entrained lighter blood components and other undesirable elements. These bowls usually operate at about 4000 to 6000 rpm.

In a typical shed blood processing system using centrifugation for washing and concentrating red blood cells, such as is described in U.S. application Ser. No. 08/036,430, shed blood from the surgical site flows into an intermediate holding reservoir under negative pressure provided by a vacuum source. When the amount of blood in the holding reservoir has reached a desired level, the blood is drawn from the holding reservoir by a peristaltic pump, and propelled through the pump and into a centrifuge bowl. Rotation of the centrifuge bowl segregates undesirable elements and concentrates the red blood cells in the bowl. After stopping rotation of the bowl, the red blood cells are removed by operation of the peristaltic pump in reverse mode to draw the cells out of the bowl, back through the pump and into a reinfusion bag from which the red blood cells can be returned to the patient by simple gravity-fed infusion.

Several minor variations based to this approach have been disclosed. For example, the vacuum action may also draw anticoagulant into the fluid stream, as in U.S. Pat. Nos. 4,668,214 and 5,234,403. Transfer from the holding reservoir to the washing apparatus may be accomplished by gravity rather than by the action of a pump, as described in U.S. Pat. No. 5,215,519 and published PCT Application No. 89/01792. A filter may be incorporated into the system at any of several locations, as in U.S. Pat. Nos. 5,311,908 and 5,234,403.

However, in all of these systems the initial collection of shed blood and its subsequent transfer to the centrifuge bowl for processing are performed separately, using physically distinct components. Intermediate reservoirs between the patient and the centrifuge bowl are used both in filling and emptying the bowl, and the system may even employ a supplementary pump, in addition to the vacuum source used for draining the surgical site. Allowing for retrieval of the concentrated red blood cells without dismounting the bowl further requires that such a supplementary pump be bidirectional. This multiplicity of pumps and reservoirs is costly and inefficient.

DESCRIPTION OF THE INVENTION

OBJECTS OF THE INVENTION

It is, accordingly, an object of the present invention to provide a method and apparatus of processing shed blood for reinfusion that accomplishes all fluid transfer using a single vacuum source.

It is another object of the invention to provide a method and apparatus of processing shed blood for reinfusion that avoids the need for a supplementary pump.

It is another object of the invention to provide a method and apparatus of processing shed: blood for reinfusion that avoids the need for a holding reservoir or an intermediate reinfusion reservoir.

It is another object of the invention to provide a method and apparatus of processing shed blood for reinfusion that allows gravity-fed reinfusion of red blood cells from the centrifuge bowl to the patient without the need for a separate reinfusion reservoir.

Another object of the invention is to provide a method of processing shed blood that allows the use of lower centrifuge rotation rates.

Another object of the invention is a portable shed blood processing system operable independently of external power sources.

Yet another object of the invention is an alternative to the addition of chemical anticoagulants to shed blood for reinfusion.

BRIEF SUMMARY OF THE INVENTION

The present invention provides an integrated, portable system for recovery and reinfusion of shed blood. The system of the invention reduces the number of distinct steps and components required to collect and filter shed blood and to wash, concentrate and reinfuse red blood cells. In particular, by modifying the centrifuge bowl and locating it between the surgical site and the vacuum source the present invention allows shed blood to be collected, washed, and reinfused without additional pumps or intermediate reservoirs.

In one aspect, the invention allows all necessary fluid transfer operations to be driven by the vacuum source that implements shed blood collection from the surgical site. The placement of the centrifuge bowl between the surgical site and the vacuum connection allows shed blood to be drawn directly into the bowl without residence in any intermediate holding vessel and thus without an additional pump to transfer blood to the bowl.

Another aspect of the invention is a centrifuge bowl design that allows direct reinfusion of the red blood cells from a stationary bowl without intermediate transfer to a reinfusion reservoir. The design provides a means for making an opening in the bottom of the bowl that allows drainage of the contents from the bowl. This possibility of gravity-fed infusion eliminates the necessity for a distinct reinfusion reservoir and an associated intermediate transfer line and pump.

These two aspects are especially advantageous in combination. Reinfusion directly from the centrifuge bowl eliminates the need to remove the red blood cells to a reinfusion reservoir by reverse pumping, and since all of the fluid movement in the system is in the same general direction, it can be fully provided by the vacuum source without a complicated system of plumbing and valving.

Another aspect of the invention is the dilution of the blood by admixture of washing solution immediately upon its introduction into the system. This dilution decreases the concentration of clotting proteins in the sample being processed, thereby inhibiting clotting action without the addition of a chemical anticoagulant. Furthermore, the resulting low viscosity of the diluted blood in conjunction with long centrifugation time afforded by the invention allows red-blood cell concentration at centrifuge bowl rotation rates of 2000 to 3000 rpm. This reduced rotation rate minimizes the likelihood of red blood cell damage upon sudden deceleration as experienced when the rotation is braked at the completion of washing. The resultant reduced power requirement makes the system more amenable to battery operation, which improves the portability of the system.

In another aspect, a centrifuge bowl design incorporates a filter in the inlet tube for removal of solid debris from the blood before it is processed in the separation chamber. This combination of components allows for simplification of the overall system without any decrease in functionality.

BRIEF DESCRIPTION OF THE DRAWINGS

The foregoing discussion will be understood more readily from the following detailed description of the invention, when taken in conjunction with the accompanying drawings, in which:

FIG. 3 schematically illustrates a modification to the configuration shown in FIG. 1.

It will be appreciated that, for purposes of illustration, these figures are not necessarily drawn to scale.

DETAILED DESCRIPTION OF THE INVENTION

Figure 1:
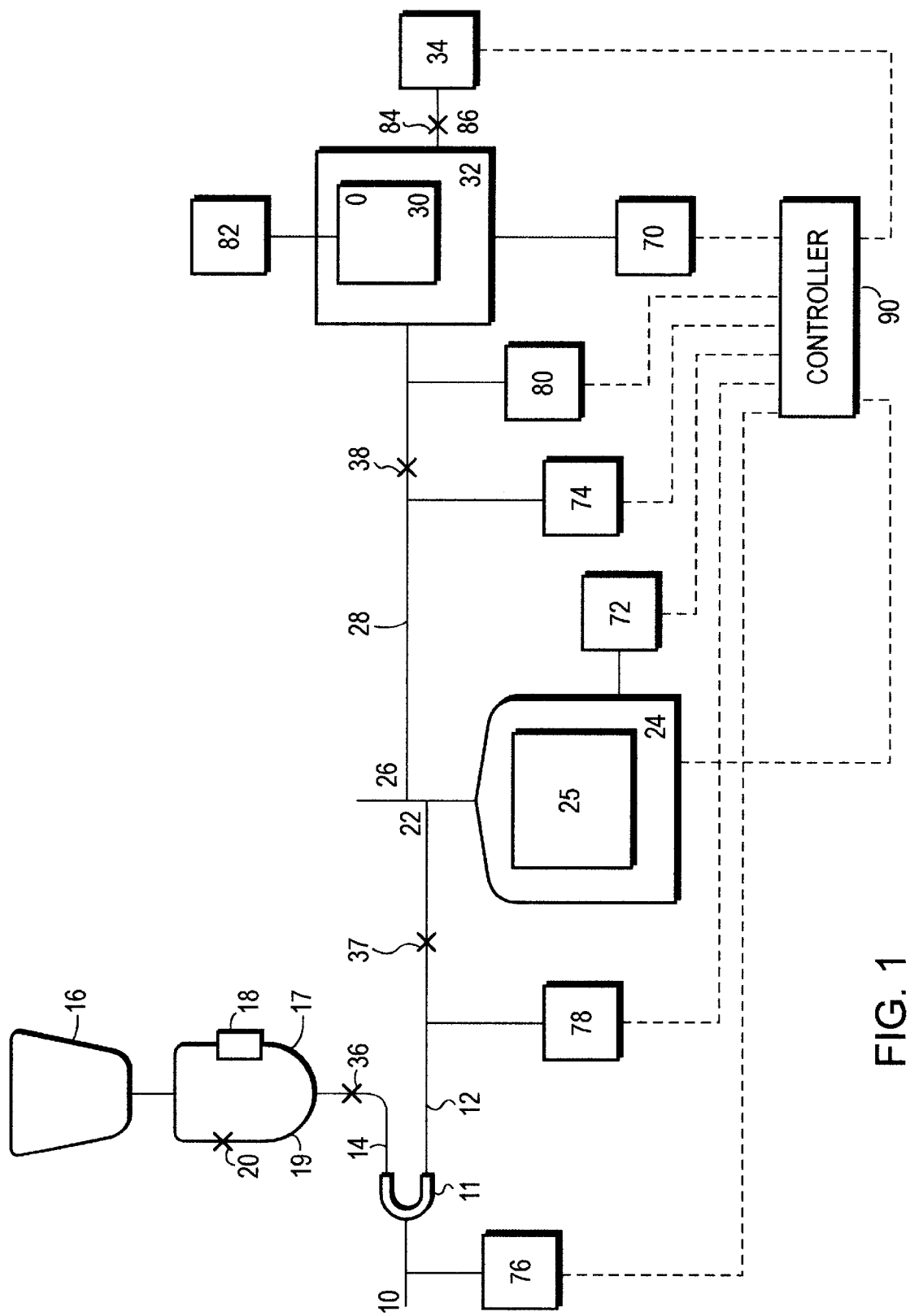
FIG. 1 schematically illustrates one blood-processing configuration of the invention.

Refer first to FIG. 1, which shows a blood-processing system according to the invention. A tube 10 collects blood from the surgical site. A coupling 11 joins tube 10 to an aspiration line 12 and a dilution line 14 that divides into two branches 17, 19. A wash solution bag 16, containing a wash solution such as normal saline or Ringer's solution, communicates fluidly with coupling 11 through divided dilution line 14. One branch 17 of the dilution line 14 comprises a flow restricter 18. The other branch 19 comprises a valve 20 such as a roller clamp. Aspiration line 12 connects to the inlet port 22 of a centrifuge bowl 25, which is itself part of a centrifuge apparatus 24 that comprises the bowl 25 and means for rotating the bowl which are not shown. The outlet port 26 of centrifuge bowl 25 is connected by an effluent line 28 to a vented waste bag 30, contained in an enclosure 32. A vacuum source 34 communicates with the interior of enclosure 32. Negative pressure applied by vacuum source 34 to the interior of the enclosure 32 is transmitted to the interior of the waste bag 30 and thereby through the effluent line 28 and the centrifuge bowl 25, to the aspiration line 12, the dilution line 14, and finally to the tube 10. A series of valves 36, 37, and 38 allow isolation of respective sections of the system, these may be, for example, ratchet clamps.

Figure 2:
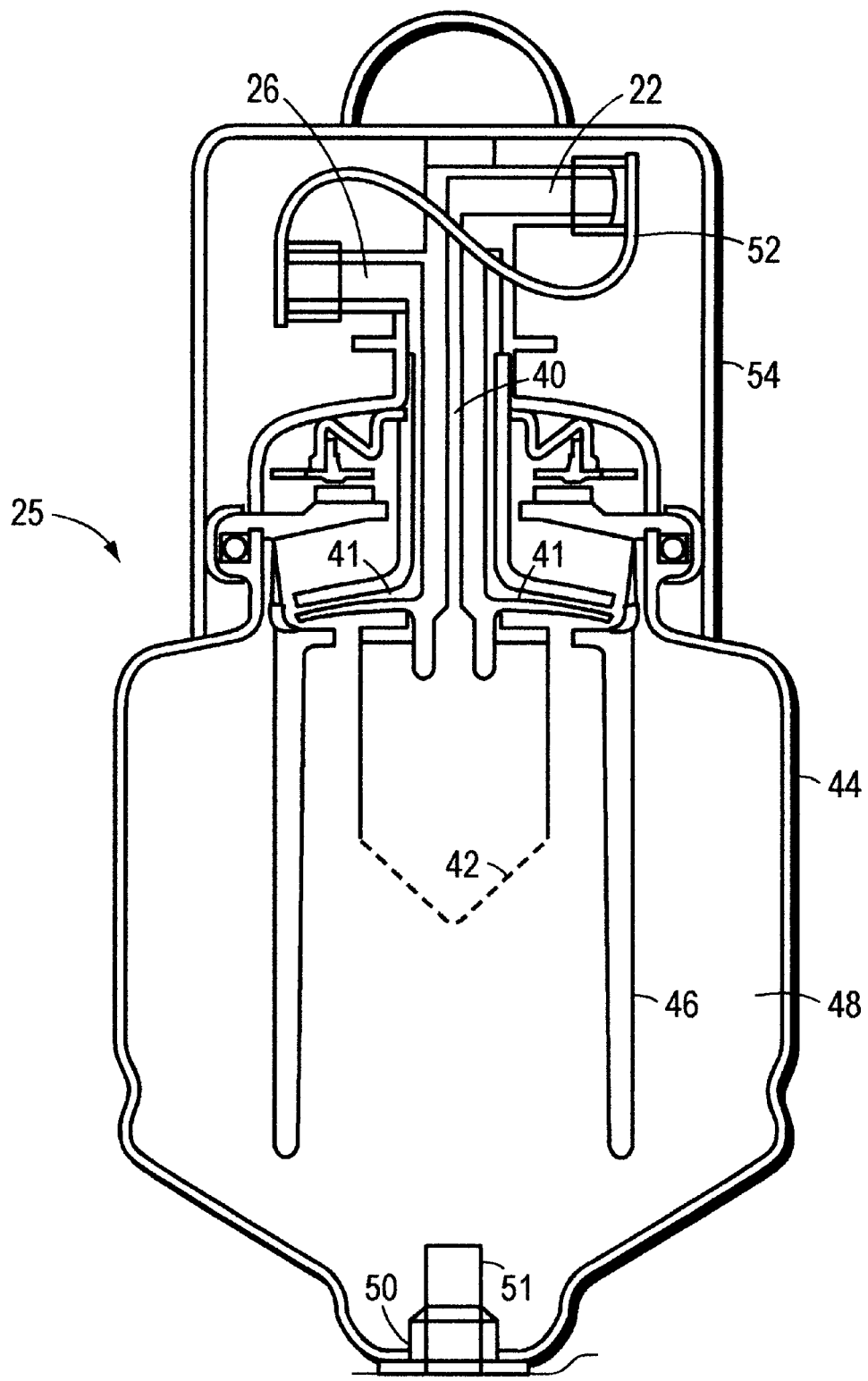
FIG. 2 is a cross section of a centrifuge bowl in accordance with the invention.

FIG. 2 shows a configuration for the centrifuge bowl 25 that is especially advantageous for use in the system shown in FIG. 1. The bowl 25 comprises a nonrotatable assembly joined to a rotatable bowl body by a rotary seal. The nonrotatable assembly comprises the inlet port 22, an inlet tube 40 extending into the bowl body from the inlet port 22, and a collection chamber 41 communicating with the output port 26. The inlet tube 40 terminates in a filter 42. The preferred pore size for the filter 42 is 180 $\mu$m. The bowl body comprises an outer wall 44 and a coaxial inner wall 46 forming a separation chamber 48 between them. An aperture 50, sealed by a female spike connector 51, in the floor of the bowl 25 permits optional drainage of the bowl contents by perforation of the spike connector 51. A pair of caps 52 cover the inlet and outlet ports when they are not in use. A cover 54 protects the nonrotatable assembly when the bowl 25 is removed from the centrifuge 24.

In operation, negative pressure from the vacuum source 34 draws blood from the surgical site through tube 10 and coupling 11 into the aspiration line 12. With the valve 20 closed, washing solution from the bag 16 is compelled by vacuum source 34 through branch 17 of the dilution line 14 at a rate controlled by the flow restricter 18, and mixes with the blood at coupling 11. This early dilution of the blood reduces its concentration of clotting proteins and prevents coagulation. The flow restricter 18 in the dilution line is calibrated to deliver a flow rate roughly equal to twice the shed blood flow rate under the applied negative pressure so that the washing solution and blood are present in the aspiration line at a ratio of at least 1.5 to 1. For example, typical postoperative blood flow rates for an orthopedic procedure are lower than 600 ml/hour. At these low flow rates and with the low viscosity resulting from the two-to-one blood dilution, a constant negative pressure of −100 to −200 mm Hg can be maintained uniformly from the waste bag 30 to the tube 10 and to the flow restricter 18 without affecting the integrity of the rotary seal or other bowl seams. An additional flush of washing solution can be obtained by opening roller clamp 20 to subject the washing solution bag to the full negative pressure in the aspiration line 12.

The diluted blood enters input port 22 and passes through the filter 42 into the separation chamber 48 of centrifuge bowl 25, which is rotating at about 2000 to 3000 rpm. The low viscosity of the diluted blood, coupled with the long centrifugation time resulting from the residence of the blood in the rotating centrifuge bowl throughout the slow fill from the surgical site, enables effective separation even at such low bowl rotation rates. The low bowl rotation rate reduces the risk to red blood cells upon bowl deceleration and consumes less power, allowing batteries to be used as the sole source of power for substantial periods of operation. Such a system is amenable to continuous operation during patient transfers and in remote locations without regard to the availability of external power sources.

As the diluted blood enters the separation chamber 48, the rotation of the bowl concentrates the red blood cells against the outer wall 44. With continued ingress of blood the supernatant, comprising lighter blood components, saline wash and debris, forms concentric layers that approach the inner wall 46 until they reach collection chamber 41 and exit out the outlet port 26. Finally, the vacuum source 34 aspirates supernatant through effluent line 28 into the waste bag 30, which is partially inflated by the pressure differential between its interior and the surrounding enclosure 32.

When bleeding at the site has ceased or when the desired volume of red blood cells has been collected in the bowl 25, the vacuum source 34 is turned off. Bowl rotation is stopped, and the bowl 25 is removed from the centrifuge 24. The inlet and outlet ports are disconnected from the aspiration and effluent lines, respectively, and capped. The spike connector 50 is then perforated to allow the bowl contents to be removed by gravity directly to the patient.

Alternatively, the vacuum driven system of the invention could be used with a conventional centrifuge bowl having no capability as a reinfusion reservoir, such as a Latham bowl, rather than with the modified bowl shown in FIG. 2. In this case, the vacuum moves the red blood cells lying at the bottom of the stationary centrifuge bowl up the inlet tube and out the inlet port. FIGS. 3A and 3B show the additional components required in order to reroute the suction so that it draws from the inlet port end of the inlet tube. An additional vacuum line 60 connects line 12 with a red blood cell receptacle 62 by means of a first three-way valve 64, and a second additional line 61 that connects receptacle 62 to line 28 by means of a second three-way valve 66. In FIG. 3A valves 64, 66 are positioned for blood collection and centrifugation. FIG. 3B shows the system during vacuum retrieval of red blood cells from the bottom of a stationary Latham bowl 68. After retrieval, the red blood cells can be reinfused directly from the receptacle 62 or processed further. A filter in the aspiration line 12 or in the vacuum line 60 would prevent entry of debris into the receptacle 62.

The invention can also be adapted for whole blood collection from donors such as for plasma pheresis. In this case, an appropriate anticoagulant solution would replace the washing solution 16, and the waste bag 30 would function as a plasma-collection bag.

Several variations of the foregoing system are consistent with the scope of the present invention. For example, the washing solution may include an anticoagulant such as heparin. The system may optionally include sensors to indicate how much blood has entered the system, such-as a gravimetric sensor 70 to read the weight of the waste bag 30 or an optical sensor 72 or 74 at the centrifuge bowl 25 or in the effluent line 28 to indicate when the bowl 25 is full of red blood cells. A sensor 76, 78, 80 and/or 82 in the tube 10, the aspiration line 12, the effluent line 28, and/or the waste bag 30, respectively, for reading pressure may be included to indicate vacuum levels injurious to red blood cells. Also, any of several mechanisms for establishing fluid communication across the floor of the centrifuge bowl 25 may be incorporated, such as spike connectors or self-sealing quick disconnect couplings. Means for regulating the delivered negative pressure may be applied to the vacuum source 34, such as a tube 84, partially open to the atmosphere as adjusted by valve 86, in the suction line between the vacuum source 34 and the enclosure 32. Operation of the centrifuge 24 and the vacuum source 34 may be effected by a programmable controller 90, which receives input from any of the aforementioned sensors and operates in accordance with predetermined criteria For example, the controller might operate these components to maintain a constant pressure or target pressure range in line 10, or to terminate collection and initiate reinfusion when bowl 25 has been filled. These control functions can be implemented without undue experimentation by those skilled in the art using conventional microprocessor circuitry and programming techniques.

It will therefore be seen that the foregoing represents a highly advantageous approach to blood processing, especially for postoperative washing and concentration of red blood cells for reinfusion. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of processing blood from a surgical site on a patient, the method comprising the steps of:
   a. providing a source of suction;
   b. providing a centrifuge including a centrifuge bowl having an inlet port, a floor, a separation chamber and an outlet port through which fluid exits the chamber;
   c. providing a receptacle;
   d. fluidly coupling the site and the inlet port;
   e. fluidly coupling the outlet port and the receptacle;
   f. coupling the suction to the outlet port through the receptacle;
   g. compelling the blood from the site into the separation chamber by means of the suction;
   h. operating the centrifuge so as to separate the blood into a plurality of components and isolate a fraction of red blood cells in the separation chamber; and
   i. conveying at least one of the components, but not the fraction of red blood cells, from the outlet port to a receptacle.

2. The method of claim 1 further comprising the steps of:
   a. providing washing solution; and
   b. introducing the washing solution into the blood so as to dilute the blood before the blood enters the centrifuge bowl.

3. The method of claim 2 wherein the step of introducing the washing solution into the blood comprises compelling the washing solution into the blood by means of the suction.

4. The method of claim 1 further comprising the steps of:
   a. stopping the operation of the centrifuge;
   b. forming an aperture in the floor of the chamber so as to allow extraction of red blood cells from the chamber; and
   c. reinfusing the isolated fraction of red blood cells into the patient through the aperture.

5. The method of claim 1 further comprising the steps of:
   a. stopping the operation of the centrifuge;
   b. applying the suction to the inlet port so as to extract a blood component from the chamber.

6. The method of claim 2 wherein the washing solution contains an anticoagulant.

7. The method of claim 1 further comprising the step of filtering the blood before the blood enters the separation chamber.

8. The method of claim 1 wherein the step of operating the centrifuge comprises rotating the centrifuge bowl at a rate lower than 4000 rpm.

9. The method of claim 1 wherein the exiting fluid is compelled to the receptacle by the suction.

10. The method of claim 2 wherein the blood is diluted by the washing solution before the blood enters the centrifuge bowl such that the solution-to-blood volume ratio is at least 1.5 to 1.

11. The method of claim 2 wherein the blood is diluted by the washing solution before the blood enters the centrifuge bowl such that the solution-to-blood volume ratio is at least 1.5 to 1.

12. The method of claim 1 wherein the centrifuge bowl comprises a filter positioned between the inlet port and the separation chamber, the blood passing through the filter before entering the separation chamber.

13. The method of claim 12 wherein the centrifuge bowl comprises an inlet tube extending into the bowl from the inlet port, the inlet tube supporting the filter.

14. The method of claim 1 further comprising the step of controlling operation of the separation chamber on the basis of at least one of:

a. negative pressure the receptacle;
   b. weight of the receptacle; and
   c. volume of red blood cells in the separation chamber.

15. The method of claim 1 further comprising the step of controlling operation of the source of suction on the basis of at least one of:

a. negative pressure in the receptacle;
   b. weight of the receptacle; and
   c. volume of red blood cells in the separation chamber.

16. The method of claim 1 wherein a first conduit couples the site and the inlet port and a second conduit couples the out let port and the receptacle.

17. The method of claim 16 further comprising the step of controlling operation of the separation chamber on the basis of at least one of:

a. negative pressure in the first or second conduit; and
   b. presence or absence of red blood cells in the second conduit.

18. The method of claim 16 further comprising the step of controlling the operation of the source of suction on the basis of at least one of:

a. negative pressure in the first or second conduit; and
   b. presence of absence of red blood cells in the second conduit.

19. A method of processing blood from a surgical site on a patient, the method comprising the steps of:

a. providing a centrifuge bowl having an inlet port, a separation chamber, a floor, and an outlet port through which fluid exits the bowl;
   b. fluidly coupling the site and the inlet port;
   c. conveying the blood from the site into the separation chamber;
   d. rotating the centrifuge bowl so as to separate the blood into a plurality of components and isolate a fraction of red blood cells in the separation chamber;
   e. stopping the rotation of the bowl;
   f. forming an aperture in the floor of the bowl so as to allow extraction of red blood cells from the bowl; and
   g. reinfusing the fraction of red blood cells into the patient through the aperture.

20. The method of claim 19 further comprising the steps of:

a. providing washing solution; and
   b. introducing the washing solution into the blood so as to dilute the blood before the blood enters the centrifuge bowl.

21. The method of claim 19 wherein the centrifuge bowl rotates at a rate lower than 4000 rpm.

22. The method of claim 20 wherein the washing solution contains an anticoagulant.

23. The method of claim 1 wherein the step of operating the centrifuge comprises rotating the centrifuge bowl at a rate between 2000 and 3000 rpm.

24. The method of claim 19 wherein the blood is diluted by the washing solution before the blood enters the centrifuge bowl such that the solution-to-blood volume ratio is at least 1.5 to 1.

25. The method of claim 19 wherein the step of rotating the centrifuge bowl comprises rotating the bowl at a rate between 2000 and 3000 rpm.

* * * * *